(12) United States Patent
Pedrizzetti et al.

(10) Patent No.: US 7,270,635 B2
(45) Date of Patent: Sep. 18, 2007

(54) FLOW-RATE CONSERVATIVE DOPPLER ESTIMATE

(75) Inventors: Gianni Pedrizzetti, Prato (IT); Emidio Marchese, Popoli (IT); Giovanni Tonti, Sulmona (IT)

(73) Assignees: Esaote S.p.A (IT); Amid SRL (IT)

( * ) Notice: Subject to any disclaimer, the term of this patent is extended or adjusted under 35 U.S.C. 154(b) by 0 days.

(21) Appl. No.: 10/506,003

(22) PCT Filed: Feb. 27, 2002

(86) PCT No.: PCT/IT02/00115

§ 371 (c)(1),
(2), (4) Date: Aug. 27, 2004

(87) PCT Pub. No.: WO03/073046

PCT Pub. Date: Sep. 4, 2003

(65) Prior Publication Data

US 2005/0107705 A1    May 19, 2005

(51) Int. Cl.
*A61B 8/06*       (2006.01)
(52) U.S. Cl. .................................................... 600/454
(58) Field of Classification Search ........ 600/454–458, 600/504–508
See application file for complete search history.

(56) References Cited

U.S. PATENT DOCUMENTS

| | | | | |
|---|---|---|---|---|
| 4,913,159 A | * | 4/1990 | Gardin et al. | 600/456 |
| 5,062,427 A | | 11/1991 | Seo et al. | |
| 6,149,595 A | * | 11/2000 | Seitz et al. | 600/438 |
| 6,719,697 B2 | * | 4/2004 | Li | 600/454 |
| 7,121,150 B2 | * | 10/2006 | Krivitski et al. | 73/861 |

FOREIGN PATENT DOCUMENTS

WO    WO 00/51495    9/2000

* cited by examiner

*Primary Examiner*—Francis J. Jaworski
(74) *Attorney, Agent, or Firm*—Woodard, Emhardt, Moriarty, McNett & Henry LLP

(57) ABSTRACT

A new method is introduced to evaluate the flow through a constriction based on Doppler data and the principle of mass conservation. This principle, properly inserted within a combination of data rearrangements allows the extraction of the complete velocity field and the optimal evaluation of the flow through the constriction. The digital implementation of the method into electronic equipments, like an echographic machine, gives an additional capability of quantifying specific valvular flows and improves diagnostic potential.

22 Claims, 5 Drawing Sheets

FLOW-RATE CONSERVATIVE DOPPLER ESTIMATE

This application is a 371 of PCT/IT02/00115 filed on Feb. 22, 2002.

TECHNICAL FIELD

Automatic processing of two- and three-dimensional echoDoppler digital data, primarily pertinent to medical imaging that improve the ability to evaluate the flow rate through a constriction on the basis of proximal Doppler imaging.

BACKGROUND ART

Quantitative hemodynamic assessment of the flow through cardiovascular valves is a matter of fundamental importance in many clinical practical aspects for diagnosis and choice of optimal therapeutic options [1-4]. A relevant example is represented by the flow that regurgitates through the mitral valve when this does not close correctly; the correct evaluation of such a regurgitant flow gives a functional measure of the actual valvular disease.

Information about the point-wise velocity in the blood are obtained by echographs that support measurements of the Doppler type, however the Doppler data acquired by echographic machines do not give explicitly, in general, values about the flow that passes through a valve and these data require a further analysis to produce an estimate of this important quantity.

Several investigators have tried to quantify the regurgitant volume and the effective regurgitant orifice using the proximal iso-velocity surface area (PISA) concept by color flow mapping and the principle of flow continuity [5-7]. The PISA method is based on the assumption that the iso-velocity contours are hemispherical proximal to the regurgitant orifice. However, this assumption is severely hampered by the complex flow fields that are present in the heart [8]. In addition, the two-dimensional color Doppler, while able to provide detailed information regarding the instantaneous velocity of flow parallel to the Doppler scan direction, is unable to represent the orthogonal components of flow velocities. Obviously, such an approach is inherently inaccurate for the estimation of the regurgitant volume.

We propose he a new method that, on the basis of the color Doppler data produced by echographic machines, is able to accurately quantify the valvular flow. The objective is to take an instantaneous two-dimensional color flow image of a valvular flow (mitral regurgitation) and evaluate the corresponding instantaneous discharge that passes through the valve.

DISCLOSURE OF THE INVENTION

We first read the two-dimensional velocity data obtained by a Doppler measure, these data are the axial (vertical) component of velocity. Let us identify a system of coordinates $\{x,z\}$ where z represents the longitudinal and x the horizontal direction parallel to the valvular plane assumed to be at z=0. Thus, the Doppler image is the map of the vertical component of velocity $v_z(x,z)$.

The valve is centered at a position $x=x_0$, and the velocity field has approximately similar parts on either side of valve centerline; the two-dimensional-velocity map is assumed to be representative of the valvular flow, i.e. it is assumed that it represents a cut centered on the valve and that no exceptional phenomena occur outside such plane (mathematically this means that a spectral decomposition in the properly defined azimuthal direction—as shown below—presents negligible intensity of even harmonics larger than zero). A typical example of velocity map (from mitral regurgitation) is show in FIG. 1.

Figure 2:
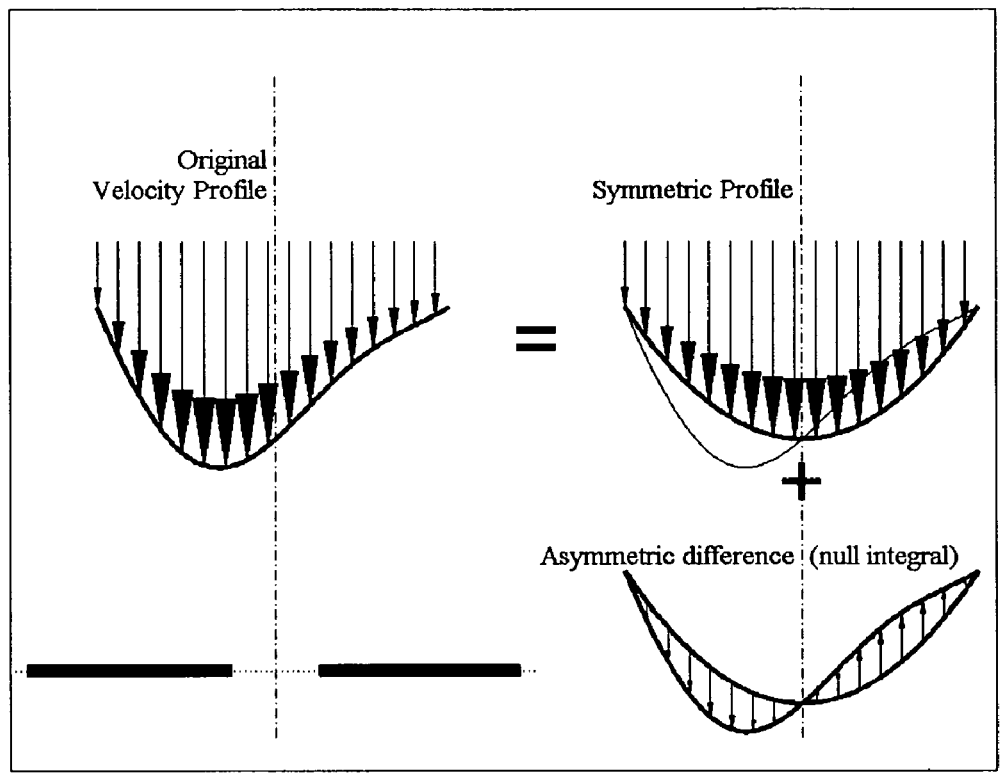
FIG. 2 is a velocity profile converging to the FIG. 1 valve as decomposed into a symmetrical profile and an asymmetrical component, the latter giving no contribution to the integral value.

The definition of a symmetry axis has relevance for the subsequent analysis. In fact, only the symmetric part of the velocity contributes to the evaluation of the flow rate, while the odd-components of the velocity give null contribution when integrated and therefore can be neglected as indicated in FIG. 2.

The optimal symmetric axis can be extracted manually, or on the basis of additional data, or estimated automatically from a maximum similarity concept between left and right velocity half-fields. The definition of a symmetry axis allows considering only the axisymmetric velocity field obtained by symmetrization of the original Doppler sampling. We can thus consider a cylindrical system of coordinates $\{r,z\}$ where r=0 represents the symmetry axis of the extracted axisymmetric velocity field $v_z(r,z)$.

The continuity equation in its differential form gives a relation between the axial variation of the axial component of velocity, $v_z(r,z)$, and the radial variation of the radial component, $v_r(r,z)$. In three-dimensional cylindrical coordinates the continuity equation reads[9,10].

$$r\frac{\partial v_z}{\partial z} + \frac{\partial rv_r}{\partial r} = 0. \qquad (1)$$

Integration of this equation along r, starting from the axis r=0 where the radial velocity is zero for symmetry reasons, allows the explicit evaluation of the radial velocity.

$$v_r(r, z) = \frac{1}{r} \int_0^r s \frac{\partial v_z}{\partial z}\bigg|_{s,z} ds. \quad (2)$$

Figure 1:
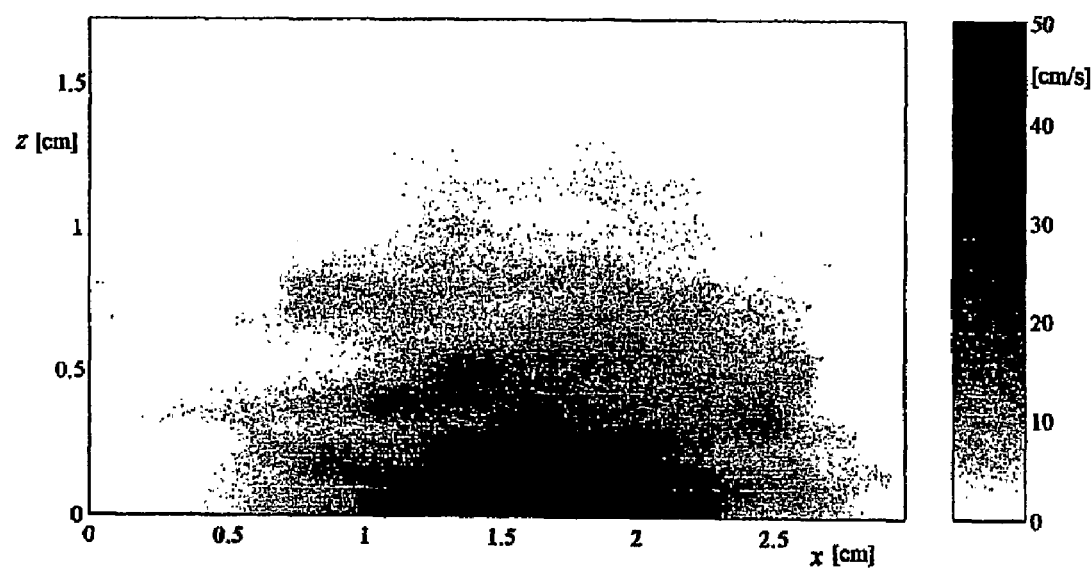
FIG. 1 is a Doppler velocity map of the flow converging to a mitral valve wherein the valve is at z=0 and the Doppler velocity component is vertical, positive downward.
Figure 3:
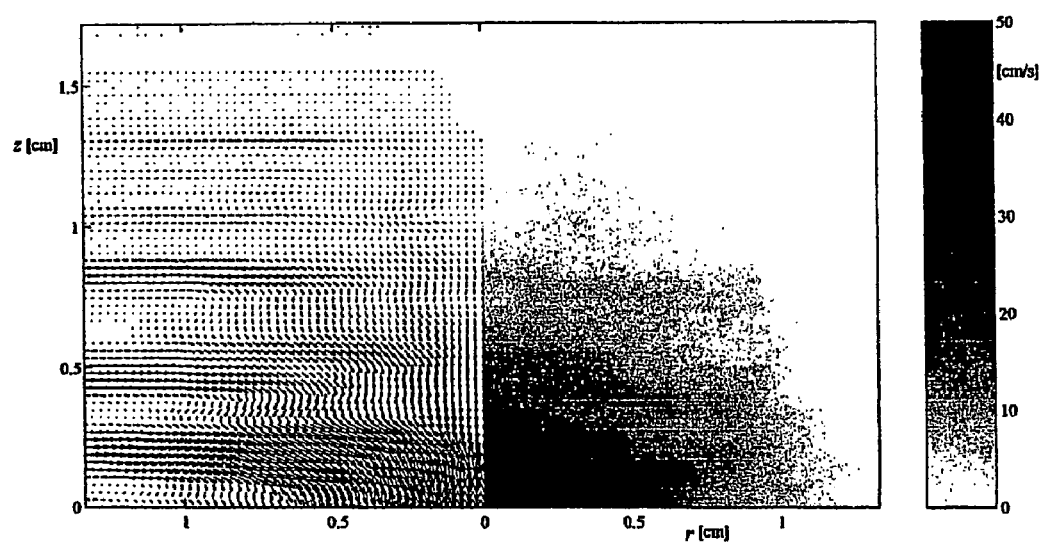
FIG. 3 is a representation of the velocity vectors (left part) as computed by a continuity equation and the symmetrical component of the Doppler velocity map (right part) based on FIG. 1.

One example of the flow corresponding to the map in FIG. 1 is show in FIG. 3.

Figure 4:
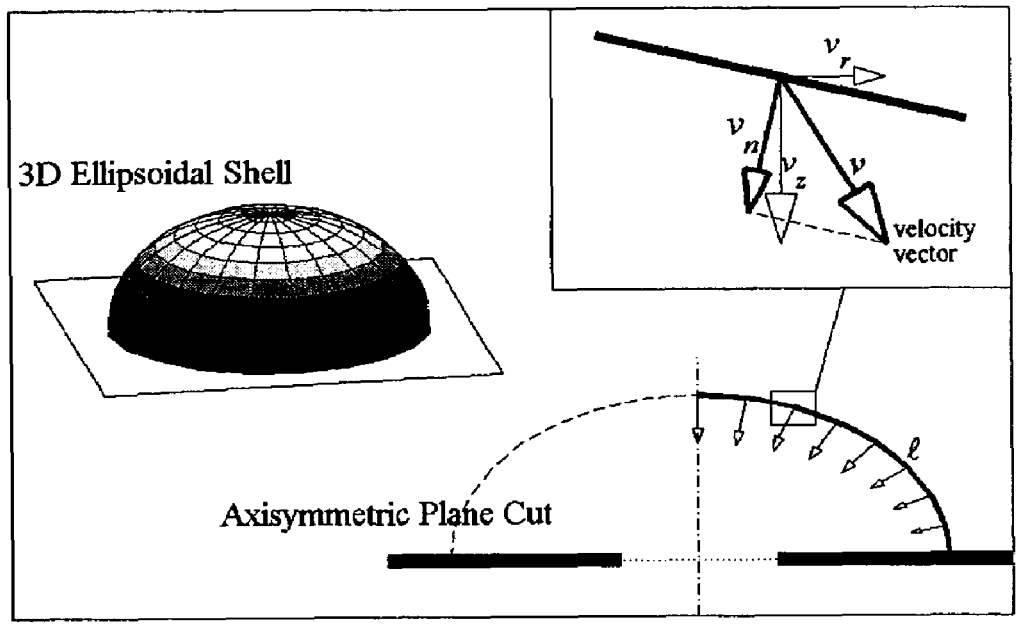
FIG. 4 is an illustration of the flow crossing an axisymmetric shell obtained by integration of the axisymmetric flow crossing a corresponding curve l on a meridian plane, wherein only the projection of the velocity vector perpendicular to the surface gives contribution to the flow.

Once the complete velocity vector field is obtained, the flow rate passing through any axisymmetric surface can be immediately evaluated. Blood being incompressible, the flow through the valve is equal to the total flow crossing any axisymmetric surface surrounding the valve. Indicating with λ the imprint-curve of the surface on a meridian plane, the flow rate Q is:

$$Q = 2\pi \int_\lambda v_n r \, d\lambda \quad (3)$$

where $v_n$ is the projection of the velocity vector in the direction normal to the curve (FIG. 4). By summating all the elementary contribution at the boundary of the control volume, we evaluate the total instantaneous flow rate Q from equation 3.

Figure 5:
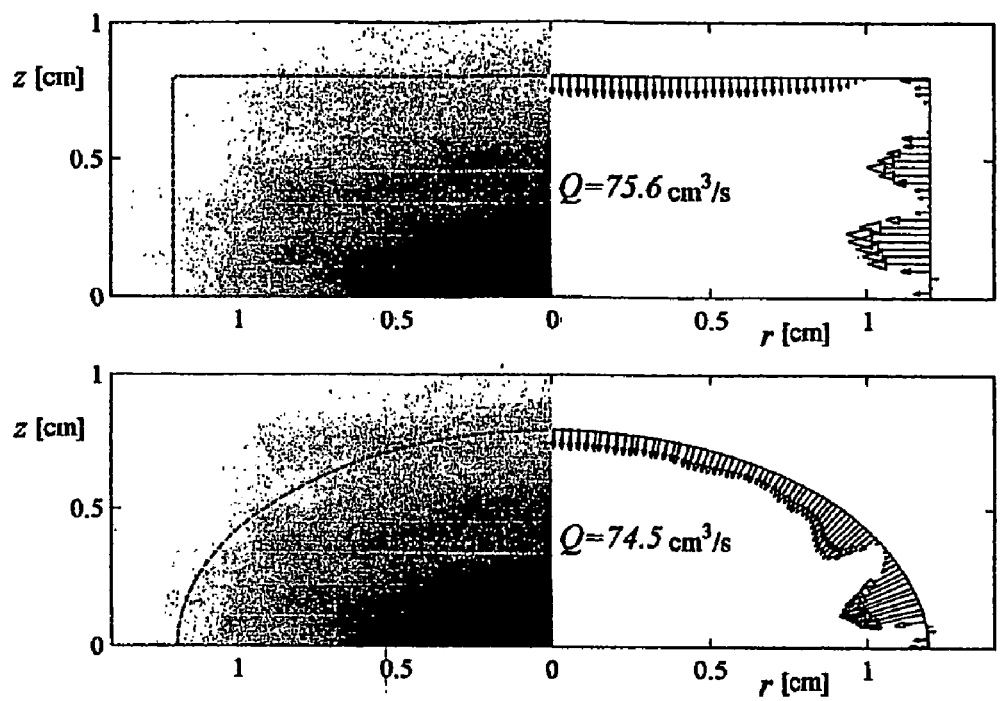
FIG. 5 illustrates a bounding surface through which the flow rate is computed, superimposed to a velocity map (left), and with a normal component of the velocity (right) wherein the flow crossing two different geometries is shown (cylinder, above, and ellipsoid, below, with the same width (12 mm) and height (8 mm)) by reporting the normal velocity vectors at the boundaries.

The result that is obtained from the velocity map of FIG. 1 is shown in FIG. 5 using two different surfaces surrounding the valve. The new method is essentially independent from the geometry and from the dimension of the control surface adopted, until this is large enough to intercept all the flow then entering the valve, and until it is small enough that the velocity values are larger than zero within the digital machine representation.

The accuracy of this method is inherently related to the "quality" and "consistency" of the image itself. The quality indicates the level of noise contained in the image. Although most mathematical passages are of integration-type that smooth out the noise, when horizontal bands noise is present this disturbance is amplified by the axial derivative appearing in equation (2), this problem can be partially circumvented by a careful evaluation of the derivatives. This new methodology resulting from the serial combination of the passages outlined above is a method that allows to evaluate the valvular flow, on the basis of the normal Doppler data measured from echographs and commonly represented in an image form. Implementation of this technique is based on numerical analysis, therefore it is transformed into a software application for its exploitation. Its translation in algorithm form is rather immediate:

1. Read the echoDoppler digital data (from image or from raw data) and obtain the Doppler velocity array $V_D(i,j)$ where i and j are the pixel indexes that span all the image in the vertical and horizontal direction.
2. Define a region of interest (ROI) for the flow proximal to the valve bounded by the valvular plane itself; obtain a reduced field $v_D(i,j)$ where the indexes i and j are now restricted to the dimension of the ROI: i=1 . . . N, j=1 . . . M.
3. Determine the optimal symmetry axis (manually of by a best likelihood techniques), thus one index $i=i_0$, and symmetrize the Doppler velocity field by $v_z(i,j)=v_D(i_0+i-1,j)/2+v_D(i_0-i+1,j)/2$ where the horizontal index i now covers the symm span: i=1 . . . . Ns.
4. Evaluate the radial component of velocity $v_r(i,j)$ by performing the integration in equation (2) with boundary condition $v_r(1,j)=0$.
5. Define one surface (or a series of them) as a sequence of L points (possibly as close as the pixel size) defined by their coordinates $(r_k, z_k)$, k=1 . . . L.
6. Evaluation of the flowrate (for any surface specified) is performed by the integral (3), and this can be achieved by several different numerical techniques. At the first order of accuracy this can be done by summation of the flow through any consecutive pair of points $(r_k, z_k)$ and $(r_{k+1}, z_{k+1})$, k=1 . . . L−1. Assume any pair as connected by a rectilinear segment, thus the normal versor is defined, the normal component of velocity can be evaluated, and the unitary contribution to (3) is evaluated.

The eventual software applications is based on the core steps outlined above, the details of the eventual product depends on the hosting equipment, the required human interface, the programmer choices, and the features of the programming language chosen for the implementation. Two Different software applications have been prepared, in two different languages, in order to start the testing of the method and its comparison with the former PISA technique. This new approach has been tested in a carefully controlled numerically generated Doppler map, with an in vitro standard equipment, and with clinical cases to verify its applicability. The results confirm the physical consistency and accuracy of the method.

BEST MODE FOR CARRYING OUT THE INVENTION

Implementation of this technique must be based on a numerical analysis (software application), therefore it should be supported in digital processing by an electronic instrument that can be the same echographic machine, or an external computer where the data are previously transferred. The procedure outlined above should be implemented through its software application into an echographic machine in order to allow the immediate evaluation of specific pathologies, like of valvular regurgitation for example. The inclusion of this additional measurement (more properly a quantification) in the echograph improves the quality of the information that can be obtained from the machine, thus giving an additional potential feature that is useful for diagnostic needs. In the case of more extensive analyses, the method has potential application into an external electronic equipment, a computer, that is equipped to read the echographic data. In this sense the computer becomes an offline system with the capability to quantify the valvular flow and eventually evaluate the severity of specific valvular diseases. This is suggested when several images or time-sequences of images must be analyzed with an effort that may not be allowed on an echograph.

REFERENCES

1. Enriquez-Sarano M, Bailey K R, Seward J B, et al. Quantitative Doppler assessment of valvular regurgitation. Circulation 1993;87:841-8.
2. Blumlein S, Bouchard A, Schiller N B, et al. Quantitation of mitral regurgitation by Doppler echocardiography. Circula-tion 1986;74:306-14.
3. Enriquez-Sarano M, Seward J B, Bailey K R, et al. Effective regurgitant orifice area: a noninvasive Doppler development of an old hemodynamic concept. J Am Coll Cardiol 1994;23:443-51.
4. Vandervoort P M, Rivera J M, Mele D, et al. Application of color Doppler flow mapping to calculate effective regurgitant orifice area: an in vitro study and initial clinical observations. Circulation 1993;88:1150-6.
5. Recusani F, Bargiggia G S, Yoganathan A P, et al. A new method for quantification of regurgitant flow rate using color Doppler flow imaging of the flow convergence region proxi-mal to a discrete orifice: an in vitro study. Circulation 1991;83:594-604.
6. Bargiggia G S, Tronconi L, Sahn D J, et al. A new method for quantitation of mitral regurgitation based on color flow Doppler imaging of flow convergence proximal to regurgitant orifice. Circulation 1991;84:1481-9.
7. Utsunomiya T, Patel D, Doshi R, et al. Can signal intensity of the continuous wave Doppler regurgitant jet estimate severity of mitral regurgitation? Am Heart J 1992; 123:166-71.
8. Walker P. G., Oyre S., Pedersen, et al. A new control volume method for calculating valvular regurgitation. Circulation 1995;92:579-586.
9. Batchelor G. K. An introduction to fluid dynamics. 1967, Cambridge University Press.
10. Pedrizzetti G. Unsteady tube flow over an expansion. J Fluid Mech 1996; 310 89-111.

The invention is claimed is:

1. A method of diagnosis of cardiovascular disease by automatic evaluation of the amount of regurgitating fluid passing through a constriction at a given instant, based on the corresponding echographic color Doppler images of the region proximal to the constriction; characterized by the steps of applying the principle of mass conservation, to the Doppler two-dimensional, or three-dimensional, instantaneous measurement of velocity on a scan plane, or scan volume, in a region proximal to the constriction and adjacent to the constriction plane; repeating the application of said principle point by point to rebuild the velocity vector field converging at said constriction and, consequently, the amount of flow converging to and passing through said constrictions; and
    using the amount of flow converging to and passing through said constriction for a part of said diagnosis.
2. The method as claimed in claim 1, applied to evaluation of the amount of fluid passing through natural or prosthetic heart valves.
3. The method as claimed in claim 1, applied to evaluation of the amount of fluid passing through a natural or prosthetic vascular constriction, i.e. a stenosis.
4. A method as claimed in claim 1 where the Doppler image is replaced by Doppler volumetric data of the region proximal to the orifice characterized by means of the same steps and substituting the symmetrical parts of a two-dimensional information with the axially symmetric part of a three-dimensional information.
5. A method of diagnosis of cardiovascular disease by automatic evaluation of the amount of fluid passing through a plane at a given instant, characterized by the steps of:
    measuring the instantaneous Doppler velocity of said fluid at a first point proximal to said plane;
    repeating said measurement for at least one additional point on a point by point basis progressively closer to said plane;
    processing said measurements in accordance with the principle of mass conservation to rebuild a velocity vector field and thereby determine the fluid volume passing through said plane; and
    using said fluid volume for a part of said diagnosis.
6. The method of claim 5, wherein said plane comprises a heart mitral valve.
7. The method of claim 5, wherein said plane comprises natural or prosthetic heart valves.
8. The method of claim 5, wherein said plane comprises a stenosis.
9. The method of claim 5, wherein said plane comprises an orifice.
10. The method of claim 5, wherein said Doppler velocity measurement may be taken in two dimensions or three dimensions.
11. A method of diagnosis of cardiovascular disease by automatic evaluation of the amount of fluid passing through an orifice, at a given instant, on the basis of corresponding echographic color Doppler images of the region proximal to the orifice; characterized by means of:
    (a) reading the velocity information from the Doppler image, said Doppler velocity being the component of the velocity vector perpendicular to an orifice plane;
    (b) dividing said Doppler velocity into its symmetrical and asymmetrical parts with respect to an orifice central axis, the symmetric part of the Doppler velocity being the only part contributing to the flow across the orifice;
    (c) applying the continuity equation to the symmetric part of the Doppler velocity on each pixel, or on rectangles of a few pixels, to evaluate the radial component of the velocity vector, the component of velocity that is perpendicular to the Doppler velocity, to obtain the symmetric part of the complete velocity vector;
    (d) applying the conversation of mass to a volume delimited by the orifice plane and an axially symmetric shell that extends from proximal region to the orifice plane;
    (e) considering an axially symmetric shell that extends from the orifice plane into the proximal region of the flow;
    (f) calculating from the symmetric part of the complete velocity vector the flow crossing the said shell, and, by the principle of conservation of mass, such flow is equal to the flow crossing the orifice; and
    (g) using the flow crossing information for a part of said diagnosis.
12. A method as claimed in claim 11 where applied to evaluation of the amount of fluid passing through natural or prosthetic heart valves.
13. A method of diagnosis of cardiovascular disease by automatic evaluation of the amount of fluid passing through a constriction, a valve, an orifice or the like, at a given instant, on the basis of Doppler imaging of the region proximal to the constriction, comprising the steps of:
    (a) reading the velocity vector perpendicular to the constriction plane from the Doppler image;
    (b) dividing said velocity vector into its symmetrical and asymmetrical parts with respect to the constriction central axis;
    (c) applying the continuity equation to the symmetric part of the Doppler velocity vector on each pixel, or on rectangles of a few pixels, to evaluate the radial component of the velocity vector thus obtaining the symmetric part of the complete velocity vector;
    (d) defining an axially symmetric shell that extends from the constriction plane into the proximal region of the flow;
    (e) calculating from the symmetric part of the complete velocity vector the flow crossing said shell which, by the principle of conversation of mass, is equal to the flow crossing the constriction; and
    (f) using the flow crossing information for a part of said diagnosis.

14. The method according to claim 13, wherein the division of the velocity vector into its symmetrical and asymmetrical parts of step (b) is achieved by an automatic estimation based on maximum similarity concept between left and right velocity half-fields.

15. The method according to claim 14, wherein step (a) further includes the step of defining a region of interest for the flow proximal to the construction bounded by the constriction plane itself and limiting the velocity vector $V_D(1,j)$ to the dimension of such region.

16. The method according to claim 15, wherein the axial components $v_z(i,j)$ of the symmetric part of the velocity vector $v_D(i,j)$ are determined through the formula:

$$v_z(i,j) = v_D(i_0+i-1,j)/2 + v_D(i_0-i+1,j)/2$$

where i and j are the pixel indexes that symmetrically span the Doppler image in the horizontal and vertical direction and $i_0$ is the index corresponding to the optimal symmetry axis determined manually and/or through best likelihood techniques.

17. The method according to claim 16, wherein the radial components of the velocity vector $V_r(i,j)$ are evaluated by performing the integration of the continuity equation.

18. The method according to claim 16, wherein the axially symmetric shell is defined by a sequence of points defined by their coordinates $(r_k, Z_k)$ with k=1, . . . , L.

19. The method according to claim 18, wherein the flowrate is approximated by summation of the flow through any consecutive pair of points $(r_k, Z_k)$ and $(r_{k+1}, Z_{k+1})$, with k−1, . . . L−1 and assuming any pair is connected by a rectilinear segment.

20. The method according to claim 13, wherein the flowrate is evaluated by the numerical calculation of the integral $$Q = 2\pi \int_l v_n r \, dl$$

wherein:

Q is the flowrate;

$v_n$ is the projection of the velocity vector in the direction normal to the curve;

r is the radial coordinate;

l is the imprint-curve of the surface on a meridian plane of the surface surrounding the valve.

21. The method according to claim 13 for the evaluation of the amount of fluid passing through natural or prosthetic heart valves or natural or prosthetic vascular constriction or through an orifice or for the amount of fluid passing through a plane at a given instant.

22. A method as claimed in claim 13 where the Doppler image is replaced by Doppler volumetric data of the region proximal to the orifice characterized by means of the same steps and substituting the symmetrical parts of a two-dimensional information with the axially symmetric part of a three-dimensional information.

* * * * *